(12) United States Patent
Perler et al.

(10) Patent No.: US 10,888,398 B2
(45) Date of Patent: Jan. 12, 2021

(54) CERAMIC IMPLANT

(71) Applicant: New Dent AG, Oensingen (CH)

(72) Inventors: Peter Perler, Port (CH); Peter Schwenter, Gerlafingen (CH)

(73) Assignee: Z-SYSTEMS AG, Oensingen (CH)

(*) Notice: Subject to any disclaimer, the term of this patent is extended or adjusted under 35 U.S.C. 154(b) by 97 days.

(21) Appl. No.: 15/471,378

(22) Filed: Mar. 28, 2017

(65) Prior Publication Data

US 2017/0196662 A1 Jul. 13, 2017

Related U.S. Application Data

(62) Division of application No. 13/504,166, filed as application No. PCT/CH2010/000275 on Nov. 4, 2010, now abandoned.

(30) Foreign Application Priority Data

Nov. 4, 2009 (CH) ..................................... 1700/09

(51) Int. Cl.
*A61C 8/00* (2006.01)
*A61F 2/30* (2006.01)
*A61C 13/00* (2006.01)

(52) U.S. Cl.
CPC .......... *A61C 8/0012* (2013.01); *A61C 8/0022* (2013.01); *A61C 13/0004* (2013.01); *A61C 13/0018* (2013.01); *A61F 2/30771* (2013.01); *A61C 2008/0046* (2013.01); *A61F 2002/3085* (2013.01); *A61F 2002/3097* (2013.01); *A61F 2002/30321* (2013.01); *A61F 2002/30906* (2013.01); *A61F 2250/0025* (2013.01)

(58) Field of Classification Search
CPC . A61C 8/0012; A61C 8/0022; A61C 13/0018; A61C 13/0004; A61C 2008/0046
USPC .................................................. 433/172–176
See application file for complete search history.

(56) References Cited

U.S. PATENT DOCUMENTS

| | | | | |
|---|---|---|---|---|
| 5,947,735 A * | 9/1999 | Day ..................... | A61C 8/0024 | 433/173 |
| 6,364,663 B1 * | 4/2002 | Dinkelacker ........ | A61C 8/0018 | 433/173 |
| 6,482,076 B1 * | 11/2002 | Straub ................ | A61F 2/30771 | 451/36 |
| 8,257,606 B2 * | 9/2012 | Stephan ............... | A61L 27/105 | 216/83 |
| 2003/0065401 A1 * | 4/2003 | Amrich .............. | A61B 17/8085 | 623/23.55 |
| 2004/0072128 A1 * | 4/2004 | Klardie ............... | A61C 8/0012 | 433/201.1 |

(Continued)

FOREIGN PATENT DOCUMENTS

DE 102006011629 9/2007
JP 07-275268 10/1995

(Continued)

*Primary Examiner* — Matthew M Nelson
(74) *Attorney, Agent, or Firm* — Rankin, Hill & Clark LLP

(57) ABSTRACT

A ceramic implant which has a ceramic, endosseous surface region that is intended to be embedded into the bone tissue and that is made of a ceramic material. The surface region has at least one first zone having a surface modification, in which first zone the surface is roughened or porous, and at least one second zone, in which the surface is not roughened or porous.

7 Claims, 3 Drawing Sheets

(56) References Cited

U.S. PATENT DOCUMENTS

| | | | | |
|---|---|---|---|---|
| 2004/0152047 A1* | 8/2004 | Odrich | | A61C 8/005 433/173 |
| 2004/0265780 A1* | 12/2004 | Robb | | A61L 27/06 433/173 |
| 2005/0227197 A1* | 10/2005 | Lin | | A61C 7/00 433/18 |
| 2006/0129161 A1* | 6/2006 | Amrich | | A61B 17/8085 606/85 |
| 2006/0246399 A1* | 11/2006 | Ehrl | | A61C 8/0012 433/201.1 |
| 2007/0111164 A1* | 5/2007 | Saade | | A61C 8/0022 433/174 |
| 2007/0112353 A1* | 5/2007 | Berckmans, III | | A61B 17/866 606/86 A |
| 2008/0014556 A1* | 1/2008 | Neumeyer | | A61C 8/0022 433/174 |
| 2008/0213728 A1* | 9/2008 | Rhew | | A61C 8/0022 433/201.1 |
| 2009/0035723 A1* | 2/2009 | Daniel | | A61L 27/50 433/215 |
| 2010/0000069 A1* | 1/2010 | Voudouris | | A61C 7/28 29/460 |
| 2010/0042223 A9* | 2/2010 | Zinger | | A61F 2/30767 623/18.11 |
| 2010/0248185 A1* | 9/2010 | Leite | | A61B 17/8071 433/173 |
| 2010/0261141 A1* | 10/2010 | Ajlouni | | A61C 8/0022 433/174 |
| 2011/0008754 A1* | 1/2011 | Bassett | | A61C 8/0012 433/175 |

FOREIGN PATENT DOCUMENTS

| | | |
|---|---|---|
| JP | 2000-166944 | 6/2000 |
| WO | 03/013383 | 2/2003 |
| WO | 03/045268 | 6/2003 |
| WO | 2004/017857 | 3/2004 |
| WO | 2005/027771 | 3/2005 |

* cited by examiner

CERAMIC IMPLANT

BACKGROUND OF THE INVENTION

Field of the Invention

The invention relates to a ceramic implant, in particular a dental implant, and to a method for producing such an implant.

Description of Related Art

Ceramic implants are known from medical technology. In particular, ceramic dental implants have become increasingly popular, among other reasons because of their property of absorbing only a small amount of visible light, as a result of which they can appear white.

In implants, the surface coming into contact with the bone is intended to fuse with the bone, i.e. the bone, in an osseointegration process, is intended to grow into surface roughnesses of the implant, such that the implant is solidly connected to the bone structurally and also functionally.

For the purpose of promoting osseointegration, both in ceramic implants and also in metal implants, a known procedure is one in which the area intended to grow into the bone is surface-modified, by means of an ablation method (in particular etching, sand blasting, water blasting, for example with abrasive particles in the water) or by means of an additive method (see, for example, WO 2005/027771), such that a desired surface roughness forms.

DE 10 2006 011 629 proposes modifying the surface of a zirconia implant by means of a laser beam. The laser beam generates linear structures in the tooth root area of the ceramic implant.

The document U.S. Pat. No. 5,947,735 relates to a self-tapping, metallic dental implant in which surface areas are treated in order to provide them with a surface roughness. However, at least one protruding cutting edge is not roughened, so that it is not made blunt by the roughening method.

The document WO 03/013383 discloses an implant which is made of titanium or ceramic and which, by means of blasting, is provided with grooves that extend at an angle to the implant axis. The implant can be stepped, in which case the different steps can have different groove structures.

A disadvantage of such methods, when applied to ceramic implants, is that they do not take account of the special material properties of ceramics. In particular, the surface treatment increases the susceptibility of the implant to a brittle fracture, since slight surface defects are caused by the treatment. These can greatly reduce the fracture resistance of the implant. This is particularly important in a load-bearing implant, for example a dental implant.

BRIEF SUMMARY OF THE INVENTION

It is an object of the invention to remedy this situation and to make available an implant and a method for producing same, which overcome the disadvantages of the prior art and, in particular, increase the fracture resistance of ceramic implants without significantly impairing the capability of osseointegration.

This object is achieved by the implant and method as are defined in the claims.

According to one aspect of the invention, a ceramic implant, in particular a dental implant, is provided which has a ceramic endosseous surface area, i.e. an area that is intended to be embedded in the bone tissue and that is made of a ceramic material. This surface area has at least a first region, with a surface modification in which the surface is roughened or porous, and at least a second region, in which the surface is not roughened or porous.

In particular, that axial partial area of the ceramic implant that has the first region/the first regions also has the second region(s) or parts thereof. That is to say, the second regions are not limited to a proximal and/or distal end area, but instead extend to axial positions at which and/or on both sides of which the first region or first regions is or are also present.

In the axial partial area comprising the first region/the first regions (i.e. an area of the implant with axial position in relation to a longitudinal axis and/or insertion axis in a certain size area, for example a middle area lying between a distal end area and the non-endosseous area), there are therefore roughened or porous surface portions and also non-roughened surface portions. In other words, the first and also the second region(s) extend across at least one common axial partial area of the endosseous area. The first and second regions engage in one another. This axial partial area is, for example, at least one part of the area provided with a thread.

This procedure means that the surface is not modified, and the implant therefore not weakened, specifically at those locations where the load-bearing cross section is particularly small or where, for other reasons, the forces are particularly great. The implant can thus be designed such that the surface of the second regions is on average at a shorter distance from the longitudinal axis than the surface of the first regions. This simple measure permits a purposeful strengthening of the ceramic implant compared to the prior art.

The first and second regions are preferably interlaced in the sense that first and second regions interchange several times along a circumferential direction and/or in particular an axially extending line; i.e. the first and second regions are not just a proximal area and a distal area. For example, the first regions extend, interrupted by the second regions, across the entire endosseous area, with the possible exception of a distal end surface or a distal end area. In all the embodiments, the first region can form a single continuous structure. This can be the case, for example, if the implant has a thread; the first region can then extend continuously along the thread crests winding helically around the endosseous area (the term "thread crests" does not specify the exact cross-sectional shape of the thread, i.e. the term also covers thread crests with flattened or rounded cross-sectional shapes). However, it is also possible that the first regions are a plurality of regions spaced apart from one another. The same also applies to the second region(s). The rest of the description refers to the first regions and second regions (in the plural); this covers embodiments with a single continuous first or second region.

For example, the first regions cover at least 20%, at least 30%, at least 40% or at least 50% of the surface of the endosseous area and, for example, at most 93%, at most 90% or at most 85%.

According to a preferred embodiment, the endosseous portion of the implant has retention and/or anti-rotation structures, for example a thread and/or a rib structure. The elevations (for example, in the case of a thread, the at least one helically extending elevation) of these retention and/or anti-rotation structures is/are designed at least partially as first regions and has/have a roughening or porous structure, whereas depressions present between this elevation/these elevations are designed as second regions and has/have no roughening or porous structure or a lesser roughening or porous structure.

Provision can therefore be made in particular that, in said partial area, the surface profile along a line in the axial direction, or possibly in the circumferential direction, appears as a plurality of elevations (for example thread crests or anti-rotation ridges) with depressions arranged therebetween. A depression is characterized in that the implant diameter is smaller locally at the site of the depression than at the site of the two adjacent elevations. The distance between the adjacent elevations and the depth of the depressions are defined by their function as retention or anti-rotation structures and are thus generally greater, for example by at least one order of magnitude, than the corresponding dimensions of the surface roughnesses added by the modification.

This procedure according to said preferred embodiment avoids a weakening originating from surface defects in the area of the depressions, i.e. where the material thickness is at its smallest. The breaking load can be deliberately increased by the measures proposed here, particularly in the case of materials with a tendency to so-called brittle fracture.

If the retention and/or anti-rotation structures are designed as a thread or comprise a thread, a surrounding area of the thread crests (for example extending into the thread flanks) is surface-modified, whereas the surface modification is not applied in the thread root.

The procedure according to the invention is advantageous particularly in ceramic dental implants or other ceramic implants with load-bearing functions. The dental implants include one-part, integral implants, but also integral multi-part implants.

Zirconia-based or alumina-based materials can be used as the ceramic material for the implant.

The endosseous implant surface area can be specifically provided with a surface modification by, for example, one of the following sequential and/or parallel methods:

Laser ablation with a focussed light beam, in particular a laser light beam (sequential). A focussed laser beam is guided along the surface such that it removes material where the first regions are intended to be formed, that is to say, for example, in the area of the thread flanks and thread crests. For example, the laser can generate trenches with islands or burrs between these, for example trenches with a depth of between 10 μm and 50 μm, for example between 10 μm and 30 μm, and a distance of between 25 μm and 300 μm. The laser is focussed specifically only on locations that belong to the first regions. In addition or alternatively, the laser beam focussing can also have a deliberately low depth of field, such that it can have an ablation effect only to a depth corresponding to the radial position of the elevations, whereas at a greater depth, i.e. at the radial position of the depressions of the implant, it is already defocussed to the extent that it can no longer have an ablation effect. If this measure is taken, the laser can also be guided in trajectories that lead across the entire surface of the endosseous portion of the implant. Because of the less focussed laser radiation, the second regions may then experience slight modifications at their surface; however, the effect of these is slight compared to the surface modifications of the first regions.

Laser ablation or other method acting from a defined direction (such as sand blasting, water blasting with abrasive media, etc.), such that the second regions lie in shadow (sequential or parallel). For example, the beam can impinge from an angle of ca. 45° to the implant axis if the flank angle of the thread is 60°, as a result of which the thread root lies in shadow. Generally, the angle of impact is preferably chosen as smaller than the flank angle of retention and/or anti-rotation structures, as a result of which depressions of these structures lie in the core shadow, wherein greater angles different than 90° also have an effect, because the depressions then lie in the half-shadow. In this embodiment too, a laser light beam can be guided with focussing along trajectories that lead substantially across the entire endosseous portion; this procedure can be supplemented by a focussing with a limited depth of field.

Ablation methods or additive methods using a mask. A mask can be placed in the depressions, for example by a selective method or by squeegee techniques or the like. Corresponding ablation methods can be used, for example etching (parallel) or, with a given stability of the mask, also laser ablation, sand blasting, water blasting with abrasive media, etc. (sequential or parallel). An example of an additive method is found in WO 2004/017857.

Combinations of these methods are also possible, for example laser ablation with a subsequent etching aftertreatment.

"Laser ablation" is generally carried out with a laser light source, although other very strong light sources are in principle not to be ruled out, for example superluminescence light sources or flashlight sources. Here, of course, "light source" not only designates radiation sources emitting in the visible range, but generally also sources of electromagnetic radiation, particularly in the visible and infrared range, and also sources of radiation of shorter wavelengths.

Implants of the type according to the invention are, for example, fully ceramic. They can be produced, for example, from a material which consists principally of zirconia, for example with at least 90% $ZrO_2$, and to which other constituents can also be admixed, for example yttrium oxide and/or hafnium oxide and/or small amounts of alumina and/or silica and/or further oxides or other constituents. Alternatively to this, the material can also consist principally of alumina or a zirconia/alumina mixture, possibly also with additives. Other ceramic materials are also conceivable.

A maximum peak-to-valley height (maximum height of the Profile; Rt) of the first regions is, for example, between 0.5 μm and 50 μm, preferably between 3 μm and 15 μm. An average peak-to-valley height (average roughness Ra) of the first regions is, for example, between 0.2 μm and 50 μm or between 0.5 μm and 30 μm, preferably between 0.8 μm and 15 μm or between 1 μm and 10 μm. When using the laser ablation method with a focussed laser beam, the peak-to-valley height can be formed by regularly arranged trenches, where the trenches can have a width of, for example, between 10 μm and 40 μm and an average spacing of between 15 μm and 60 μm.

A maximum peak-to-valley height of the second regions is, for example, at most 3 μm, at most 2 μm, at most 1.5 μm or at most 1 μm; an average peak-to-valley height of the second regions is, for example, 1 μm or less, in particular less than 0.5 μm. The average roughness Ra of the second regions is significantly less than the average roughness of the first regions and is preferably between 0.02 and 0.5 μm, particularly preferably less than 0.3 μm.

In addition to the first and second surface regions formed by the ceramic material, the endosseous area can additionally have other surface regions formed by other materials. For example, thermoplastic surface regions according to WO 2004/017857 may be present. Express reference is made here to the teaching of said document, insofar as the latter relates to load-bearing implants and, in particular, dental implants.

The surface of the implant, of the endosseous portion, or also only of the first regions, can be aftertreated, for example by silanization or hydroxylation, as a result of which the osseointegrative action is strengthened.

BRIEF DESCRIPTION OF THE DRAWINGS

Embodiments of the invention are explained in more detail below with reference to the figures. In the figures, identical reference signs denote identical or analogous elements. In said figures.

DETAILED DESCRIPTION OF THE INVENTION

Figure 1:
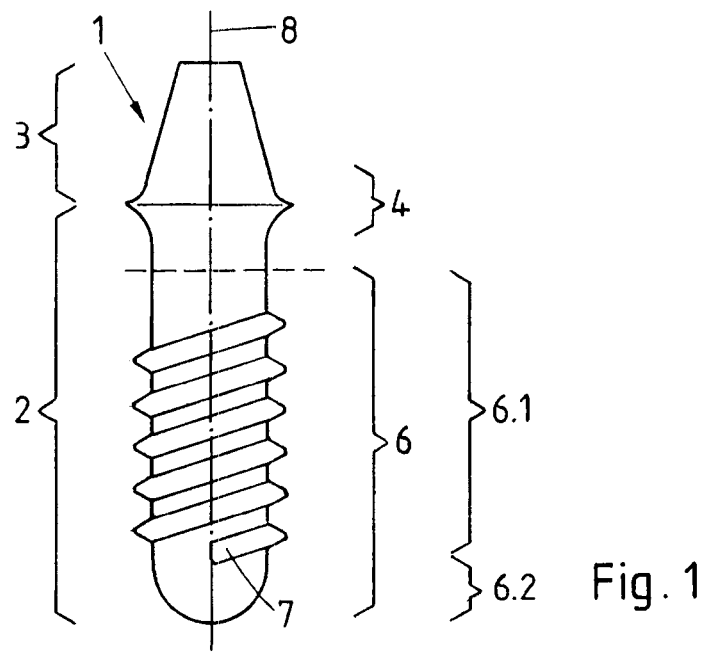
FIG. 1 shows a schematic view of a dental implant with a thread as retention structure.

The implant 1 according to FIG. 1 is fully ceramic and, for example, produced mainly from zirconia. It has an anchoring portion 2 and, formed in one piece with the latter, an abutment portion 3 for attachment of a crown (not shown). The abutment portion can also be used for application of a screwing-in tool during the implantation. For example, it has, in a manner known per se, a structure deviating from the cylinder symmetry, such that the crown or the screwing-in tool can be connected to the abutment for rotation therewith.

In the area of the transition between the anchoring portion 2 and the abutment portion 3, the implant has a widening 4 which, for example, can form a shoulder that is supported on and seals the gum after implantation.

A distal area of the anchoring portion 2, making up a large part of the latter, forms the endosseous area 6 which, after the implantation, is surrounded by bone tissue. After the implantation, the bone tissue grows into surface structures of the endosseous area 6. In the endosseous area, there is a thread 7 which, after the implantation, ensures the necessary primary stability and also contributes to the permanent anchoring of the implant. The endosseous area 6 can be divided up into a first endosseous partial area 6.1 and a second endosseous partial area 6.2 (end area). The first endosseous partial area 6.1 has the thread. It must be load-bearing and must also be anchored in such a way as to take up forces. It has the first regions and also the second regions. The second endosseous partial area 6.2 is a distal end area. It can have a roughened and/or non-roughened surface.

FIG. 1 likewise indicates the longitudinal axis 8 (or insertion axis) which, as is known per se, can be an axis of symmetry (wherein the symmetry is interrupted by the thread) of the endosseous area 6 or even of the entire implant. However, the implant does not necessarily have to be symmetrical.

According to the invention, the endosseous area 6 now has first, modified surface regions with a deliberately induced surface roughness, and second, unmodified surface regions in which the surface roughness is slight, i.e. the surface is smooth. The surface property of the second surface regions is generally determined by the method by which the implant is brought to its shape. The modified, first surface regions have greater roughness compared to the first surface regions.

In the embodiment according to FIG. 1, the first regions comprise the crests and upper flank areas of the thread; the second regions comprise the thread root. Parts of the endosseous area where the thread is not present (in this case the distal, rounded end, and the neck portion between the thread and the widening 4) can be designed as second regions or preferably at least partially as first regions.

Figure 2:
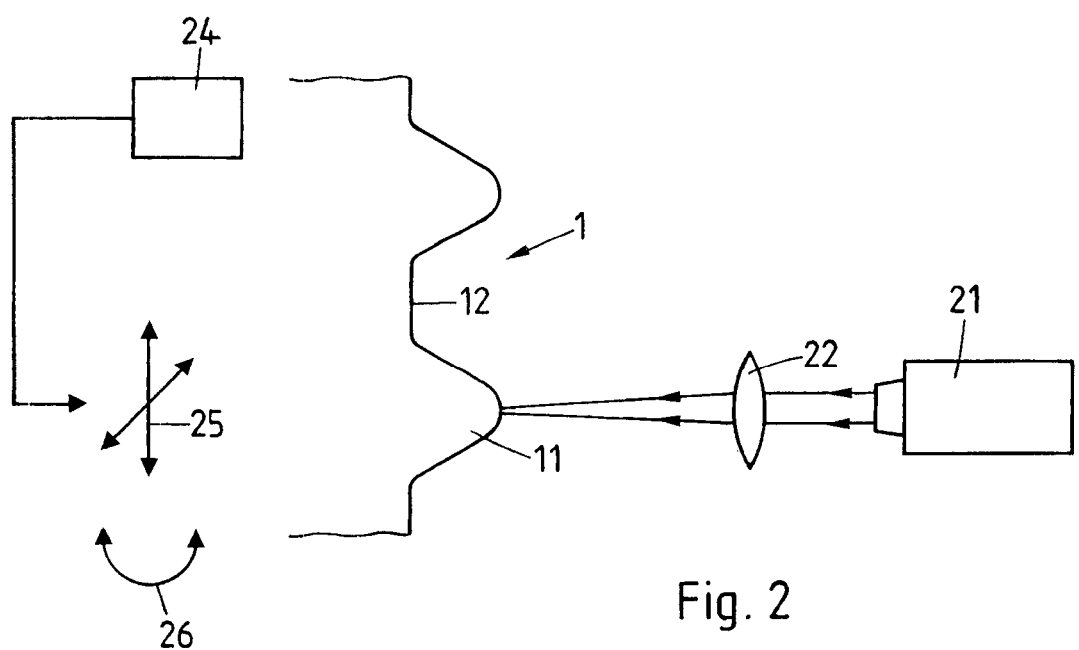
FIG. 2 shows a schematic view of a first surface modification method.

FIG. 2 is a very schematic view showing a method for applying the surface modification in a sequential method with a focussed light beam. The beam from a suitable laser light source 21, for example a high-power solid-state laser, in particular an Nd:YAG laser or an Er:YAG laser, is focussed on the surface of the pre-shaped implant 1; the diameter of the focus can be ca. 5 μm at the narrowest point. Under the control of a control system 24, the implant, on the one hand, and the laser light source 21 with the focussing means 22, on the other hand, are moved relative to each other, as is indicated by the arrows 25, 26, which represent a translation movement and a rotation movement, respectively. The movement takes place in such a way that, in total, a multiplicity of trenches with a width of ca. 20 μm and a depth of ca. 20 μm are formed in the first regions 11, the distance from trench to trench, measured from trench center to trench center, can be ca. 40 μm. This therefore results in oriented surface roughnesses. In addition to the effect of the known and randomly formed surface roughnesses, this has the further effect that collagen structures of the ingrowing bone tissue can align themselves along the trenches.

In the procedure according to FIG. 2, the following measures can be taken alone or in combination, such that the surface modification is performed only in the first regions:

The control system 24 controls the laser and the movement means such that the laser acts only on surface sections that correspond to the first regions or belong to the latter. For this purpose, the three-dimensional structure of the implant 1 and its position must be programmed in exactly.

The laser is focussed such that it has a comparatively low depth of field, for example of ca. 50-100 μm. Such focussing is easily possible. The axis of the implant then has a fixed distance to the laser and to the focussing means, and the light beam is then focussed on a radial position of the implant, which corresponds to the position of the elevations. The laser light beam can then also optionally be guided in trajectories across the entire surface of the endosseous portion.

Figure 3:
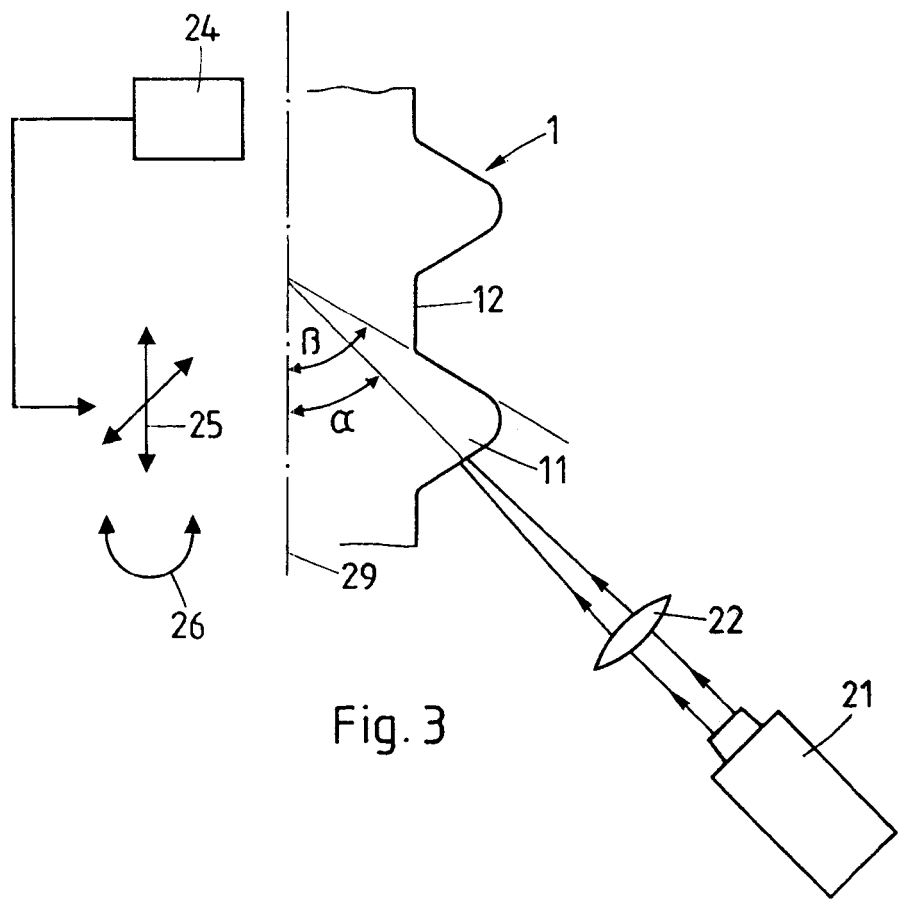
FIG. 3 shows a schematic view of a second surface modification method.

FIG. 3 is a schematic view of an ablation method with a laser beam, in which method the thread root remains in shadow, as a result of which the surface roughness is obtained only on the flanks and peaks. To ensure that the thread root 12 is in shadow, the angle α of the direction of incidence with respect to the implant axis should be smaller than the angle β of the thread flanks implant axis. In the figure, an axis 29 is indicated, which is parallel to the implant axis (not shown). For example, the angle α can be approximately 45° and the flank angle ca. 60°, as a result of which the angle β is also approximately 60°.

An effect is achieved even at angles of incidence a that do not fully correspond to the above condition, for example where α≈β.

Also in the procedure according to FIG. 3, the laser light beam can optionally be guided in trajectories across the entire surface of the endosseous portion, as a result of which the exact 3D geometry of the implant does not have to be recorded and programmed in the control system. Alternatively, however, the control system can also be programmed such that, in order to supplement the selectivity, it additionally only operates the laser when the laser beam impinges on surface areas that belong to the first regions, or such that the laser beam is only in fact guided across such surface areas at all.

A method analogous to FIG. 3 is also possible with alternative oriented ablation methods, in which methods there is generally much less pronounced focussing, as a result of which the relative movement of the implant with respect to the source of the oriented ablation medium in some cases only has to be a helical movement or even just a rotation movement about the axis.

Figure 4:
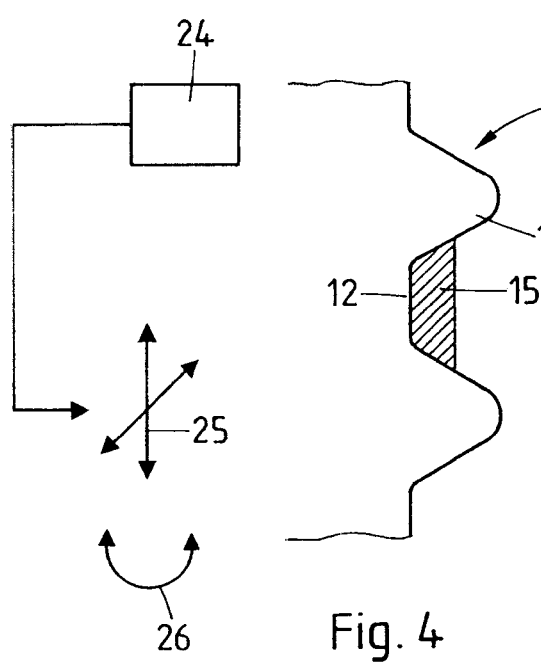
FIG. 4 likewise shows a schematic view of a masking technique for further surface modification methods.

FIG. 4 shows, again schematically, the masking technique. The thread root 12 is covered by a mask 15. A parallel ablation method (for example etching) or additive method can then ensure the surface modification at the uncovered locations. The mask can be made of a suitable resist material, which can be removed again subsequent to the surface modification method.

Figure 5:
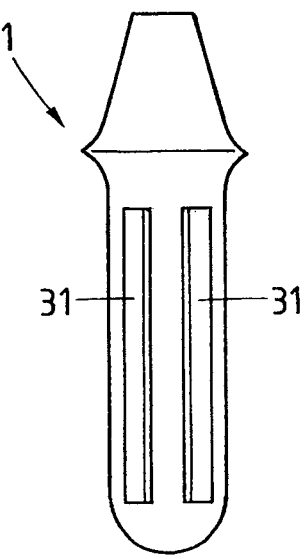
FIG. 5 shows a schematic view of a dental implant with anti-rotation structures.

FIG. 5, finally, shows an implant 1 which has axially extending anti-rotation structures 31 instead of a thread. The implant can have additional means (not shown) for producing primary stability or, in a departure from the embodiment shown, can be of the two-part type.

In an implant with anti-rotation structures instead of a thread, it is also possible to apply the principle that the first surface regions are arranged in the area of elevations and the second surface regions are arranged in the area of depressions lying between these elevations. The same applies to implants with further retention structures in addition to or instead of anti-rotation structures.

EXAMPLE

A zirconia dental implant with less than 10% yttrium oxide and provided with a thread was produced in a conventional manner in which a shaped body made of the ceramic material was produced in a press sintering method and was then brought by grinding to the desired shape with thread. The ceramic material used is an yttria-stabilized tetragonal partially crystalline zirconia. The zirconia ceramic used meets the standard ISO 13356:2008 to "Implants for Surgery—Ceramic Materials based on yttria-stabilized tetragonal zirconia (Y-TZP)".

In the area of the thread crests and thread flanks, the surface was then deliberately modified using an Nd:YAG solid-state laser (wavelength 1064 nm) with an output power of 20 watt, pulsed 5 to 100 kHz, working distance 100 mm and a focus spot of 2 to 10 μm. For this purpose, the laser focussed to a focus with a diameter of 5 μm and with a low depth of field was guided across the surface in such a way that a multiplicity of trenches with a width of ca. 20 μm and a depth of ca. 20 μm were formed, the distance from trench to trench being ca. 40 μm. No surface modification was carried out in the area of the thread root. Electron microscope measurements were performed on the resulting dental implant.

FIGS. 6-9 show a selection of the corresponding electron microscope images. The images were taken with an electron beam of 20 kV.

Figure 6:
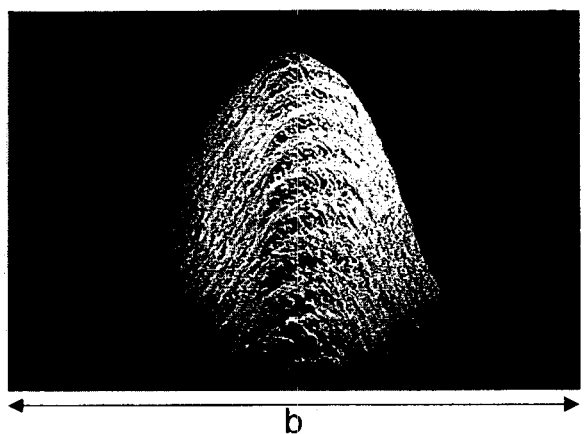
FIGS. 6-9 show electron microscope images of the surface of a dental implant designed according to the invention.
Figure 7:
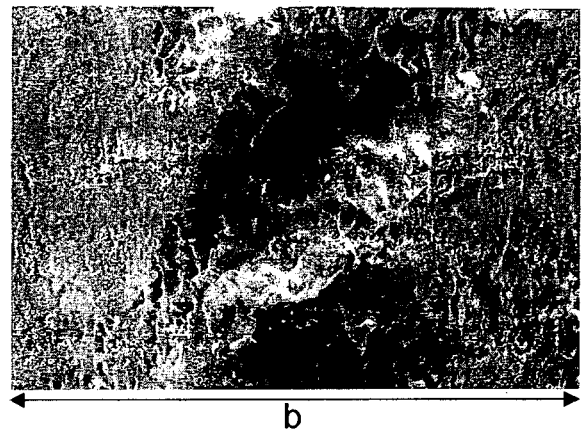
Figure 8:
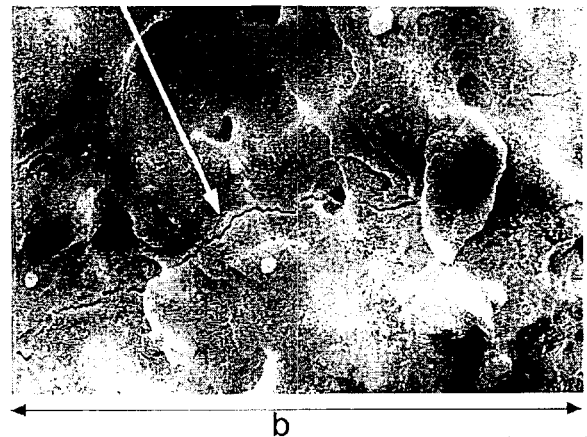
Figure 9:
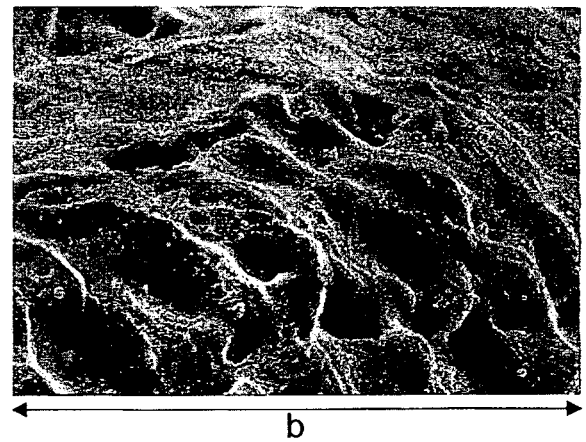

FIG. 6 shows the thread crest with the clearly visible trenches at regular intervals. The whole width b of the area shown in FIG. 6 corresponds to 700 μm. FIG. 7 shows a detail in a perpendicular view and at greater resolution (with b=200 μm); a valley can be seen between two elevations. FIG. 8 shows a detail of the valley at a still greater resolution; it shows very clearly the surface defects typical of surface modification methods and in the form of fissures (bright arrow). FIG. 9 shows at the same scale as FIG. 9 (in each case b=50 μm), but from a slightly oblique viewing angle, a detail of the thread root without surface modification; there are hardly any surface defects visible.

What is claimed is:

1. A method for producing a dental implant, wherein the dental implant has a ceramic endosseous surface area of an endosseous portion, comprising the steps of:
   in a first step, providing the implant having an intended shape, which includes the ceramic endosseous surface area, said ceramic endosseous surface area comprising a thread having a first region and a second region, wherein said first region comprises crests and upper flank areas of the thread and the second region comprises a thread root, which is disposed between said upper flank areas of said thread and,
   in a second step, modifying said ceramic endosseous surface area in order to obtain a roughening or porous structure for promoting osseointegration,
   wherein in the second step, the implant surface is modified in said first region of the thread to a first extent, whereas said second region of the thread is not modified, or is modified to a second extent, said second extent being less than said first extent.

2. The method as claimed in claim 1, wherein the second step of modifying the ceramic endosseous surface area comprises directed ablation medium.

3. The method as claimed in claim 2, wherein the directed ablation medium is a laser beam, as a result of which the surface modification is performed with a focused laser beam.

4. The method as claimed in claim 3, wherein the laser is focused such that a depth of field is less than a height of characteristic elevations in an area of the ceramic endosseous surface area.

5. The method as claimed in claim 3, wherein a movement of the focused laser beam, relative to the implant, and an output of the laser beam are controlled such that the laser beam has a substantially ablating action only at locations belonging to the first region.

6. The method as claimed in claim 2, wherein the direction from which the medium acts is at a smaller angle ($\alpha$), to an axis of the implant, than a maximum angle of slope ($\beta$), to the implant axis, of elevations of the first region of the thread, as a result of which these elevations cast a shadow on depressions defined by the second region of the thread.

7. The method as claimed in claim 1, wherein in the second step, the second region is covered by a mask.

* * * * *